(12) United States Patent
Yamane et al.

(10) Patent No.: US 8,986,913 B2
(45) Date of Patent: Mar. 24, 2015

(54) METHOD AND APPARATUS FOR INSPECTING A MASK SUBSTRATE FOR DEFECTS, METHOD OF MANUFACTURING A PHOTOMASK, AND METHOD OF MANUFACTURING A SEMICONDUCTOR DEVICE

(71) Applicants: Kabushiki Kaisha Toshiba, Tokyo (JP); Tsuneo Terasawa, Tokyo (JP)

(72) Inventors: Takeshi Yamane, Tsukuba (JP); Tsuneo Terasawa, Ome (JP)

(73) Assignees: Kabushiki Kaisha Toshiba, Tokyo (JP); Dai Nippon Printing Co., Ltd., Tokyo (JP)

( * ) Notice: Subject to any disclaimer, the term of this patent is extended or adjusted under 35 U.S.C. 154(b) by 96 days.

(21) Appl. No.: 13/840,489

(22) Filed: Mar. 15, 2013

(65) Prior Publication Data
US 2013/0244142 A1 Sep. 19, 2013

(30) Foreign Application Priority Data

Mar. 15, 2012 (JP) ................. 2012-059421

(51) Int. Cl.
  G03F 1/24 (2012.01)
  G01N 21/956 (2006.01)
  G03F 1/00 (2012.01)
(52) U.S. Cl.
  CPC ............... *G01N 21/956* (2013.01); *G03F 1/00* (2013.01); *G03F 1/24* (2013.01); *G01N 2021/95676* (2013.01)
  USPC .......... 430/5; 382/144; 356/237.2; 356/237.5
(58) Field of Classification Search
  CPC ........... G03F 1/00; G03F 1/24; G01N 21/956; G01N 2021/95676
  USPC .................. 430/5; 382/144; 356/237.2, 237.5
  See application file for complete search history.

(56) References Cited

U.S. PATENT DOCUMENTS

| 6,646,281 B1 | 11/2003 | Krantz et al. |
| 2003/0067598 A1 | 4/2003 | Tomie |
| 2009/0091752 A1 | 4/2009 | Terasawa et al. |

FOREIGN PATENT DOCUMENTS

| JP | 4-328549 | 11/1992 |
| JP | 6-235624 | 8/1994 |
| JP | 3068636 | 5/2000 |
| JP | 2005-514670 | 5/2005 |
| JP | 3728495 | 10/2005 |
| JP | 2006-266943 | 10/2006 |
| JP | 2009-74825 | 4/2009 |
| JP | 2009-92407 | 4/2009 |

OTHER PUBLICATIONS

English-language abstract of JP 4-114162, filed Apr. 15, 1992.

*Primary Examiner* — Christopher Young
(74) *Attorney, Agent, or Firm* — Finnegan, Henderson, Farabow, Garrett & Dunner, LLPC

(57) ABSTRACT

According to one embodiment, a method of inspecting a mask substrate for defects, includes acquiring a defocus image of a partial region of a mask substrate using a dark-field optical system, acquiring a just-focus image of the partial region using the dark-field optical system, generating a set composed of first signals obtained from the defocus image and having signal intensities equal to or higher than a first threshold value, excluding, from the set, the first signals pertaining to parts in which signal intensities of signals obtained from the just-focus image are equal to or higher than a second threshold value, determining an inspection threshold value for signal intensities, on the basis of the first signals not excluded from, and remaining in, the sea.

6 Claims, 4 Drawing Sheets

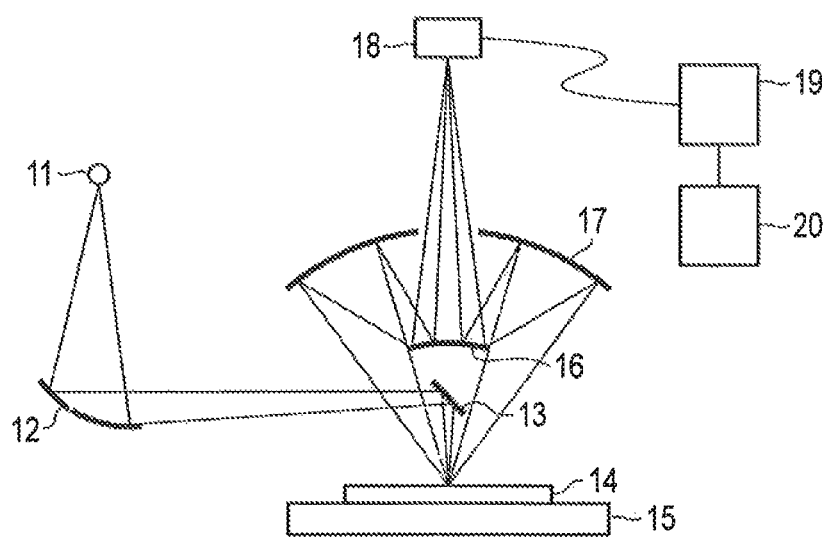
F I G. 1
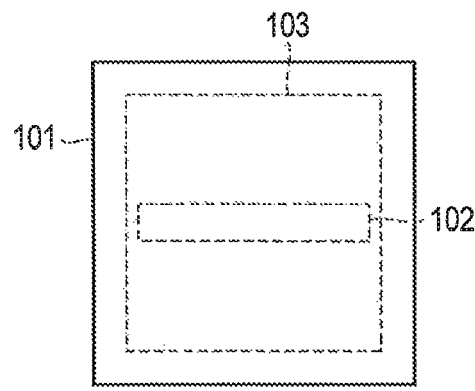
F I G. 3
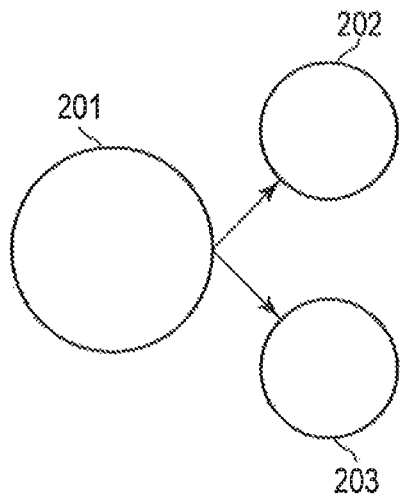
F I G. 4

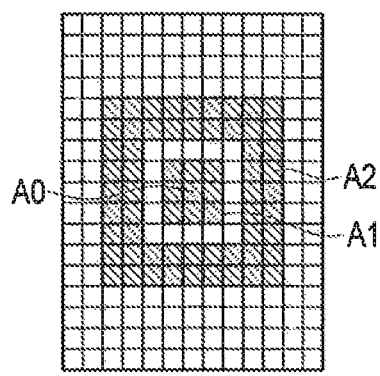
F I G. 7
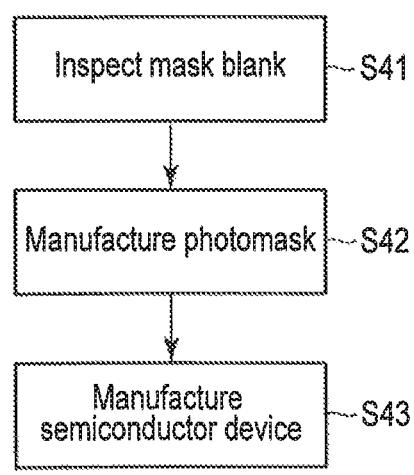
F I G. 8

METHOD AND APPARATUS FOR INSPECTING A MASK SUBSTRATE FOR DEFECTS, METHOD OF MANUFACTURING A PHOTOMASK, AND METHOD OF MANUFACTURING A SEMICONDUCTOR DEVICE

CROSS-REFERENCE TO RELATED APPLICATIONS

This application is based upon and claims the benefit of priority from Japanese Patent Application No. 2012-059421, filed Mar. 15, 2012, the entire contents of which are incorporated herein by reference.

FIELD

Embodiments described herein relate generally to a method of inspecting a mask substrate for defects, and the like.

BACKGROUND

If a mask blank has defects, the mask pattern formed on a photomask cannot be correctly transferred to a semiconductor substrate. It is therefore important to inspect the mask blank before the photomask is prepared.

A method of inspecting a mask blank for defects is known, in which a dark-field optical system acquires dark-field images. If the mask blank has defects, intense scattered light will emanate from the defects. In any dark-field image, the defects are observed as bright points. Hence, in order to detect a defect signal, a threshold level is set, and any signal having a level higher than the threshold level is regarded as a defect signal.

In the course of the inspection, however, noise signals may be detected, erroneously as defect signals. For example, if the threshold level is too low, weak defect signals can be detected, but a frequency of (the number of) erroneously detecting noise signals increases. On the other hand, if the threshold level is too high, fewer noise signals are detected, but defect signals having intensity lower than the threshold level cannot be detected.

Thus, it has hitherto been difficult to detect noise signals accurately in the process of inspecting the mask substrate (e.g., mask blank) for defects. It has inevitably hard to inspect, with high reliability, the mask substrate for defects.

BRIEF DESCRIPTION OF THE DRAWINGS

FIG. 1 is a diagram schematically showing the configuration of an apparatus according to an embodiment, which is configured to inspect a mask substrate for defects;

FIG. 3 is a diagram showing a partial region of a mask blank and an inspection region of the mask blank;

FIG. 4 is a diagram showing a set of signals stored in a storage unit;

FIG. 7 is a diagram showing a modification of the embodiment; and

FIG. 8 is a flowchart showing a method of manufacturing a photomask and a method of manufacturing a semiconductor device.

DETAILED DESCRIPTION

Figure 2:
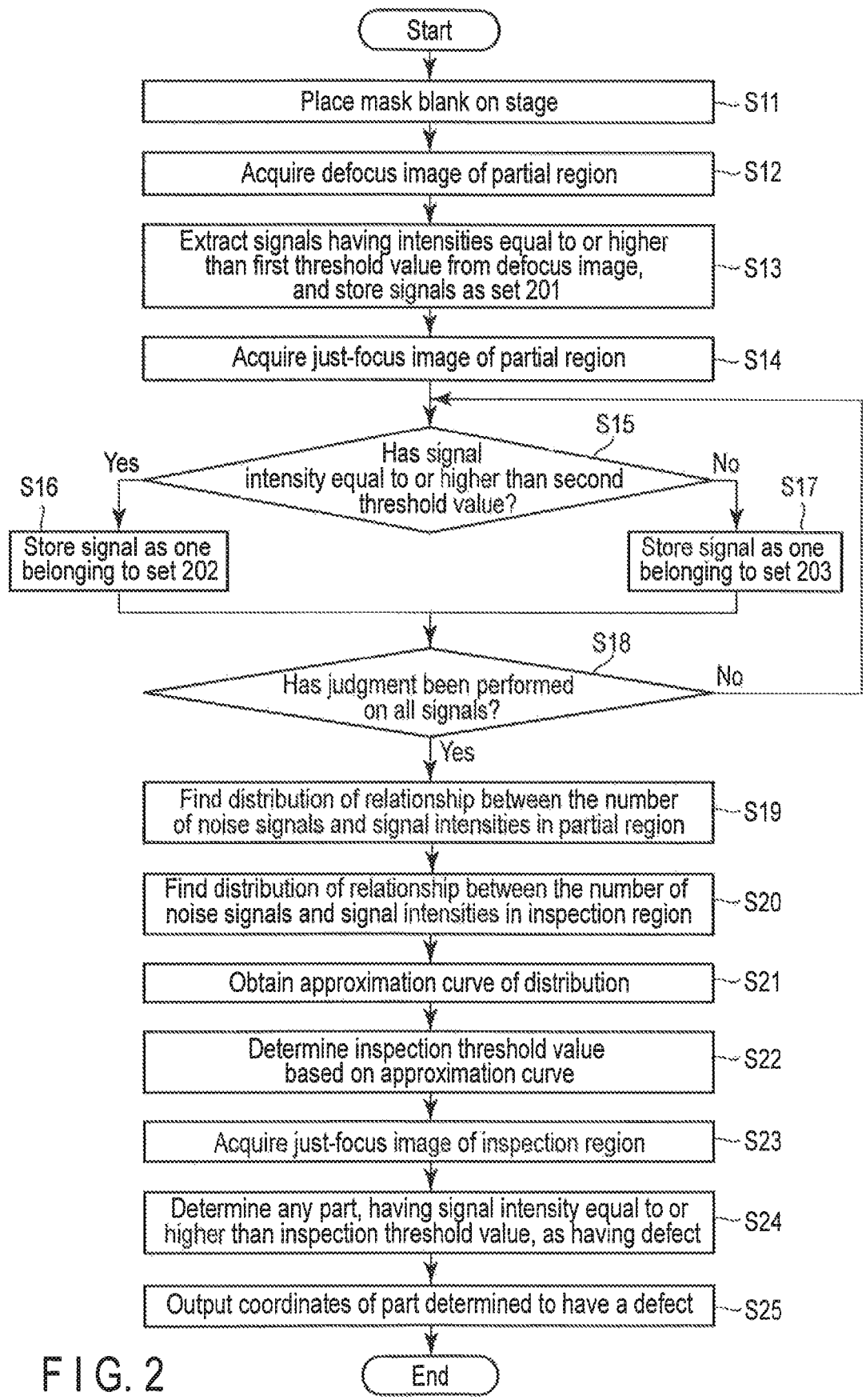
FIG. 2 is a flowchart showing a method according to the embodiment, which is designed to inspect a mask substrate for defects.

In general, according to one embodiment, a method of inspecting a mask substrate for defects, the method comprising: acquiring a defocus image of a partial region of a mask substrate using a dark-field optical system; acquiring a just-focus image of the partial region of the mask substrate using the dark-field optical system; generating a set composed of first signals obtained from the defocus image and having signal intensities equal to or higher than a first threshold value; excluding, from the set, the first signals pertaining to parts in which signal intensities of signals obtained from the just-focus image are equal to or higher than a second threshold value; determining an inspection threshold value for signal intensities, on the basis of the first signals not excluded from, and remaining in, the set; acquiring an image of an inspection region of the mask substrate using the dark-field optical system; and determining, based on the image of the inspection region, that any part having a signal intensity equal to or higher than the inspection threshold value has a defect.

The embodiment will be described below, with reference to the accompanying drawings.

FIG. 1 is a diagram schematically showing the configuration of an apparatus according to an embodiment, which is configured to inspect a mask substrate for defects.

The extreme ultraviolet (EUV) light emanating from a light source 11 is applied via an elliptical mirror 12 and a planer mirror 13 to a mask substrate 14. In this embodiment, the mask substrate is a mask blank. The mask blank 14 is a mask blank for a reflection-type photomask used for EUV exposure. More specifically, the mask blank 14 has a multilayer reflection film formed on a glass substrate. The mask blank 14 is placed on a stage 15 that can be moved in X direction, Y direction and Z direction.

The light applied to the mask blank 14 is scattered at the surface of the mask blank 14. Any light beam with a radiation angle smaller than a prescribed angle is shielded by a shielding unit (i.e., convex mirror) 16. Any light beam with a radiation angle larger than the prescribed angle is collected by a concave mirror 17 and applied to the shielding unit (i.e., convex mirror) 16. Any light beam coming from shielding unit (i.e., convex mirror) 16 is focused at the imaging surface of a time-delay integration (TDI) camera 18. The optical system descried above is a dark-field optical system. The TDI camera 18 therefore takes a dark-field image.

The signal based on the image obtained by the TDI camera 18 is supplied to a personal computer 19 that functions as an operation unit. The personal computer 19 performs an operation for determining defects. The personal computer 19 is connected to a storage unit 20. The storage unit 20 stores the signal based on the image obtained by the TDI camera 18.

FIG. 2 is a flowchart showing a method according to the embodiment, which is designed to inspect a mask substrate for defects. The method of inspecting the substrate for defects will be explained with reference to the flowchart of FIG. 2.

First, the mask blank 14 is placed on the stage 15 (S11). The mask blank 14 placed on the stage 15 is moved to the defocus position. The defocus position is spaced from the just-focus position by such a distance that relatively small defects (non-coarse defects), if any on the surface of the mask blank 14, are riot focused at the TDI camera 18. More precisely, the distance between the just-focus position and the defocus position is preferably about 30 times $\lambda/NA^2$ (where $\lambda$ is the wavelength of the exposure light and NA is the numerical aperture of the optical system).

After moving the mask blank 14 to the defocus position, the dark-field optical system is used, acquiring a defocus image of a partial region included in the mask blank 14 (i.e., region included in the pattern-formation surface of the mask blank 14) (S12). FIG. 3 is a diagram schematically showing the positional relation between the mask blank 14 and the partial region. In FIG. 3, number 101 designates the mask blank, number 102 designates the partial region, and number 103 designates an inspection region, which will be described later. The defocus image is acquired by the TDI camera 18. The image acquired by the TDI camera 18 is obtained as sets composed of the intensities of signals acquired at the respective pixels of the TDI camera 18 and the coordinates.

Of the signals obtained from the defocus image, the signals having intensities equal to or higher than a first threshold value are extracted (S13). A set of signals (first signals) having intensities equal to or larger than the first threshold value is thereby generated. The set of signals, so generated, is stored in the storage unit 20 as a set 201 (S13). The first threshold value is sufficiently smaller than an inspection threshold value, which will be descried later. Ordinary defects (non-coarse defects) existing on the mask blank 14 are not extracted from the defocus image. Therefore, any signal detected in this step, having intensity higher than the first threshold value, has derived from a. noise or a coarse defect.

Next, the mask blank 14 placed on the stage 15 is moved to the just-focus position. Then, the dark-field optical system is used, acquiring a just-focus image of the partial region 102 on the mask blank 14 (S14). In the just-focus image, the signals resulting from coarse defects have far higher intensities than the noise signals.

Then, it is determined (S15) whether any signal having intensity higher than a second threshold value exists in a region near the coordinates of the signal (having intensity higher than the first threshold value) included in the set 201 stored in Step S13. Assume that the second threshold value is larger than the intensity of any noise signal and far smaller than the intensity of any signal resulting from a coarse defect. Also assume that the region near the coordinates has a size falling within coordinate errors.

If the signal has intensity equal to or higher than the second threshold value, it is determined to have derived from a coarse defect, and is stored in the storage unit 20, as a signal belonging to a set 202 shown in FIG. 4 (S16). As a result, a part, for which the signal generated from the defocus image has intensity equal to or higher than the first threshold value and the signal generated from the just-defocus image has intensity equal to or higher than the second threshold value, is extracted from the partial region. Further, the signal pertaining to that part is stored in the storage unit 20, as belonging to the set 202.

If the signal does not have intensity equal to or higher than the second threshold value, it is determined to have derived from noise. In this case, the signal is stored in the storage unit 20, as a signal belonging to a set 203 (S17).

Further, Steps S15 to S17 are repeated for all signals included in the set 201 shown in FIG. 4 (S18).

As the steps described above are performed, any signals generated from the just-focus image and having intensities equal to or higher than the second threshold value are excluded from the set 201, and a set 202 composed of the excluded signals is obtained. The signals remaining, not excluding from the set 201, constitute a set 203.

Next, with respect to the signals (noise signals) included in the set 203 shown in FIG. 4, the relationship between a certain signal intensity and the number of signals having intensities equal to or higher than the certain signal intensity are plotted. As a result, such a distribution of the number of noise signals and the signal intensities is obtained in the partial region, as indicated by plot P1 in FIG. 5 (S19). Plot P1 shown in FIG. 5 indicates the number of signals having intensities equal to or higher than the certain signal intensity with respect to the certain signal intensity on the horizontal axis of FIG. 5. That is, plot P1 shows the number of positions where the signal intensity is equal to or higher than the certain value.

Figure 5:
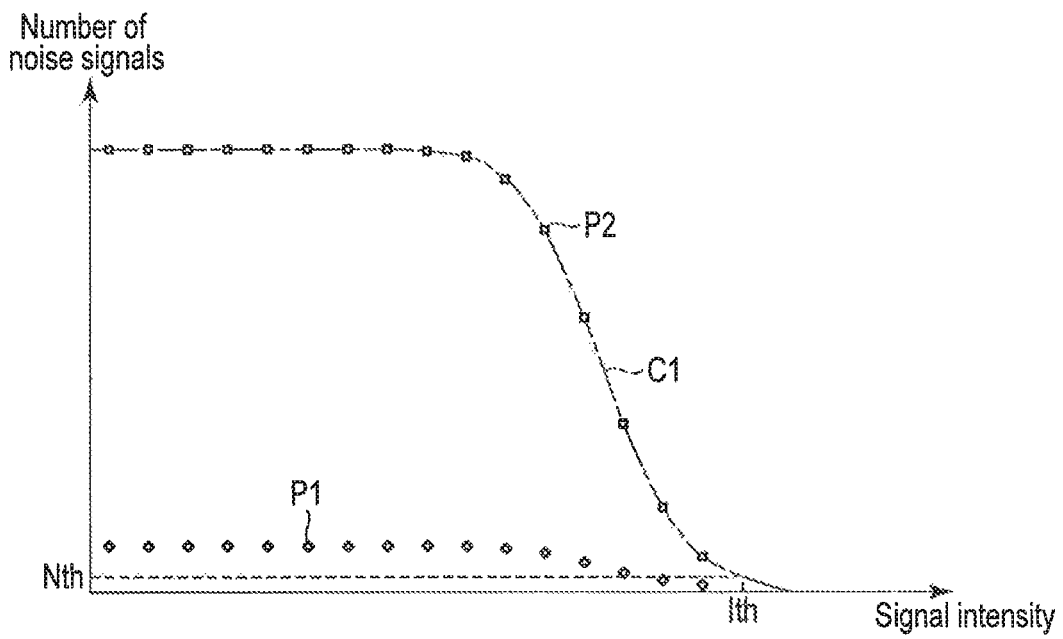
FIG. 5 is a diagram showing distribution of the number of noise signals and signal intensities.

Then, the distribution of FIG. 5 (plot P1) is used, determining a distribution of the number of noise signals and the signal intensities in a desired inspection region (i.e., region 103 shown in FIG. 3) (S20). To be more specific, the area of the image acquiring region is considered proportional to the number of noise signals of the image acquiring region. The area ratio of the inspection region 103 to the partial region 102 is therefore calculated, and plot P1 shown in FIG. 5 is multiplied the area ratio. The distribution of the number of noise signals and signal intensities in the inspection region 103 is thereby determined, as plot 92 shown in FIG. 5.

Further, fitting approximation is performed by using a given function, on the distribution of the number of noise signals and the signal intensities (i.e., plot P2) in the inspection region. Such an approximation curve C1 as shown in FIG. 5 is thereby obtained (S21).

Next, used on the approximation curve C1 shown in FIG. 5, in the inspection region 103, the signal intensity which is obtained when the number of signals (the number of parts) of the vertical axis of FIG. 5 is equal to or lower than a target value (prescribed value) Nth is determined as inspection threshold value Ith (S22). The target value Nth is an expected value of a tolerable detection number of noise signals. If one noise is allowed in ten inspections, the target value Nth is 0.1.

The inspection threshold value Ith of the signal intensity is thus determined on the basis of the signals constituting the set 203, which remain in the set 201 or have not been excluded from the set 201.

The mask blank 14 is moved to the just-focus position. The dark-field optical system is used, acquiring a just-focus image of the inspection region 103 at the surface of the mask blank 14 (S23).

Based on the image of the inspection region 103, it is determined that any part, which has signal intensity equal to or higher than the inspection threshold value Ith, has a defect (S24).

Figure 6:
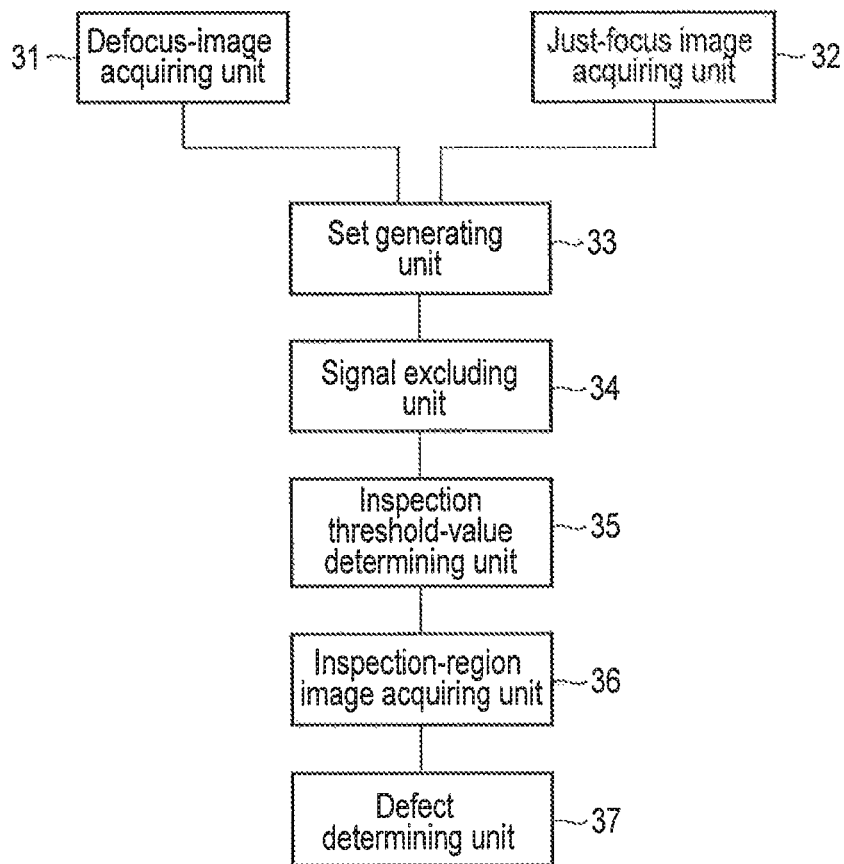
FIG. 6 is a function block diagram showing a configuration that performs various processes according in the embodiment.

Next, the coordinates of the part which has been determined to have a defect, are output (S25). If no parts are determined to have a defect, in Step S24, data indicating that no defects have been detected is output FIG. 6 is a function block diagram showing the configuration that performs various processes described above. The processes are performed by mainly the personal computer 19.

The configuration of FIG. 6 comprises a defocus-image acquiring unit 31, a just-focus image acquiring unit 32, a set generating unit 33, a signal excluding unit 34, an inspection threshold-value determining unit 35, an inspection-region image acquiring unit 36, and a defect determining unit 37.

The defocus-image acquiring unit 31 is configured to use the dark-field optical system, acquiring a defocus image of a partial region of the mask substrate. The just-focus image acquiring unit 32 uses the dark-field optical system, acquiring a just-focus image of the partial region of the mask substrate. The set generating unit 33 is configured to generate a set of first signals, each being acquired from the defocus image and each having signal intensity equal to or higher than the first threshold value. The signal excluding unit 34 is configured to exclude, from the set, any first signal at a part in which a signal intensity of a signal acquired from the just-focus image is equal to or higher than the second threshold value. The inspection threshold-value determining unit 35 is configured to determine the inspection threshold value for signal intensity, based on the first signal remaining in the set, or not excluded from the set. The inspection-region image acquiring unit 36 is configured to use the dark-field optical system, acquiring the image of the inspection region of the mask substrate. The defect determining unit 37 is configured to determine that any part which has signal intensity equal to or higher than the inspection threshold value, has a defect. These components perform the functions already specified above.

In this embodiment described above, a set of first signals generated from a defocus image and having signal intensities equal to or higher than the first threshold value is generated. First signal at a part in which signal intensity of a signal acquired from the just-focus image is equal to or higher than the second threshold value, is excluded from the set. Then, the inspection threshold value of signal intensities is determined based on the first signals not excluded from the set, or remaining in the set. It is therefore possible to detect only the noise signals from which the signals resulting from coarse defects have been excluded. Then, the inspection threshold value of the signal intensities is determined based on the noise signals. The threshold value for the noise signals generated during the defect inspection can therefore be appropriately determined, and the noise signals can be reliably detected. As a result, the mask substrate, such as mask blank, can be inspected for defects, with high reliability.

In the embodiment described above, the intensity distribution of illumination light may not be negligible, and the level change of the defect signal, resulting from the intensity difference between the illumination light components, may not be negligible. In this case, the region surrounding a region of interest may be taken into consideration. More precisely, the average signal intensity measured in the region outside the region of interest is subtracted from the signal intensity measured at the region of interest, and the resulting signal intensity may be used as signal intensity for the signal derived from the defocus image or just-focus image. The use of the above described method can reduce the influence of the intensity distribution of the illumination light.

FIG. 7 is a diagram showing the example described above. As shown in FIG. 7, the pixel A0 of interest is the center pixel of a 9×9 pixel region. In this pixel region, all pixels, but the inner 5×5 pixel, define a region A2. The average signal intensity of the region A2 is used as background level. Further, the background level of the region A2 is subtracted from the signal intensity of each pixel of a 3×3 pixel region A1, in which the pixel A0 of interest is the center pixel. The sum of the differences, each between the signal intensity of each pixel and the background level, of the region A2, is defined as peak intensity. The region A1 (i.e., 3×3 pixel region in the embodiment) preferably has a size that is equivalent to the resolution of the focusing optical system, or equivalent to the signal expansion caused by electron diffusion in the TDI camera, Preferably, the region A2 is sufficiently larger than the above-mentioned signal expansion.

In the embodiment described above, the mask substrate is a mask blank. Nonetheless, the method described above can be also applied to any mask substrate other than a mask blank. The method can be applied to, for example, a photomask having a cyclic pattern such as line-and-space pattern. Fine line-and-space pattern of a specific cycle has many lines and many spaces in each pixel of the TDI camera. Hence, the signal intensity for each pixel is considered constant if the mask substrate does not have a defect. The method described above can therefore detect defects of the photomask.

The method according to the embodiment can be applied to a method of manufacturing a photomask and also to a method of manufacturing a semiconductor device.

FIG. 8 is a flowchart showing a method of manufacturing a photomask and a method of manufacturing a semiconductor device. First, a mask blank is inspected by the method explained above (S41). Next, using the mask blank inspected, a photomask is manufactured (S42). Further, using the photomask so manufactured, a semiconductor device is manufactured (S43). More specifically, the mask pattern (i.e., circuit pattern) formed on the photomask is transferred to the photoresist provided on a semiconductor substrate. Then, the photoresist is developed, forming a photoresist pattern. Further, using the photoresist pattern as mask, conductive films, insulating films or semiconductor films are etched.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An apparatus for inspecting a mask substrate for defects, the apparatus comprising:
    a stage configured to place a mask substrate;
    a dark-field optical system configured to acquire an image of the mask substrate placed on the stage;
    a defocus-image acquiring unit configured to acquire a defocus image of a partial region of a mask substrate using the dark-field optical system;
    a just-focus image acquiring unit configured to acquire a just-focus image of the partial region of the mask substrate using the dark-field optical system;
    a set generating unit configured to generate a set composed of first signals obtained from the defocus image and having signal intensities equal to or higher than a first threshold value;
    a signal excluding unit configured to exclude, from the set, the first signals pertaining to parts in which signal intensities of signals obtained from the just-focus image are equal to or higher than a second threshold value;
    an inspection threshold-value determining unit configured to determine an inspection threshold value for signal intensities, on the basis of the first signals not excluded from, and remaining in, the set;
    an inspection-region image acquiring unit configured to acquire an image of an inspection region of the mask substrate using the dark-field optical system; and
    a defect determining unit configured to determine, based on the image of the inspection region, that any part having a signal intensity equal to or higher than the inspection threshold value has a defect, 2. The apparatus according to claim 1, wherein determining the inspection threshold value by the inspection threshold-value determining unit includes:
    acquiring the number of parts having a signal intensity equal to or higher than a certain value, based on the first signals not excluded from, and remaining in, the set; and determining, as the inspection threshold value, a signal intensity in a case where the number of such parts is equal to or smaller than a prescribed number.

3. The apparatus according to claim 1, wherein the mask substrate is a mask blank.

4. The apparatus according to claim 3, wherein the mask blank is a reflection-type mask blank for EUV exposure.

5. The apparatus according to claim 1, wherein at least one of the signal intensity of the signal acquired from the defocus image and the signal intensity of the signal acquired from the just-focus image corresponds to a signal intensity obtained by subtracting an average signal intensity measured in a region outside a region of interest from a signal intensity measured in the region of interest.

6. The apparatus according to claim 1, wherein the defocus image and the just-focus image are acquired by a TDI camera.

* * * * *

UNITED STATES PATENT AND TRADEMARK OFFICE
CERTIFICATE OF CORRECTION

| | | |
|---|---|---|
| PATENT NO. | : 8,986,913 B2 | Page 1 of 1 |
| APPLICATION NO. | : 13/840489 | |
| DATED | : March 24, 2015 | |
| INVENTOR(S) | : Yamane et al. | |

It is certified that error appears in the above-identified patent and that said Letters Patent is hereby corrected as shown below:

Title page, item (57) Abstract, ultimate line, change "and remaining in, the sea." to --and remaining in, the set.--

Signed and Sealed this
Twenty-first Day of July, 2015

Michelle K. Lee
*Director of the United States Patent and Trademark Office*